United States Patent [19]

Skyler et al.

[11] Patent Number: 5,422,125
[45] Date of Patent: Jun. 6, 1995

[54] METHOD AND COMPOSITION FOR TREATMENT OF INSULIN RESISTANCE SYNDROMES

[75] Inventors: Jay S. Skyler, Key Biscayne; Phillip Frost, Miami Beach; Elliot F. Hahn, North Miami Beach, all of Fla.

[73] Assignee: Baker Norton Pharmaceuticals, Inc., Miami, Fla.

[21] Appl. No.: 322,397

[22] Filed: Oct. 12, 1994

Related U.S. Application Data

[63] Continuation of Ser. No. 89,953, Jul. 12, 1993, abandoned.

[51] Int. Cl.$^6$ .............. A61K 33/26; A61K 37/26
[52] U.S. Cl. ......................... 424/646; 514/3; 514/866
[58] Field of Search ............ 514/492, 866, 3; 424/646

[56] References Cited

U.S. PATENT DOCUMENTS

| | | | |
|---|---|---|---|
| 4,217,343 | 8/1980 | Gaffar et al. | 424/48 |
| 4,343,794 | 8/1982 | Podos et al. | 424/646 |
| 4,882,171 | 11/1989 | Posner et al. | 424/616 |
| 5,023,358 | 6/1991 | Lazaro et al. | 556/42 |
| 5,164,384 | 11/1992 | Paul | 514/188 |

OTHER PUBLICATIONS

Rossetti et al. *Diabetes,* 39:1243–1250 (1990).
Rossetti et al. *J. Clin. Invest.,* 84:892–899 (1989).
Cordera et al. *Endocrinology,* 126:2177–2183 (1990).
Blondel et al. *Am. J. Physiol.,* 258:E459–E467 (1990).
Serradas et al. *Pancreas,* 6:54–62 (1991).

*Primary Examiner*—Raymond Henley, III
*Attorney, Agent, or Firm*—Kirschstein et al.

[57] ABSTRACT

A method of treating human or animal patients suffering from insulin resistance syndromes, particularly diabetes mellitus, by administering an effective amount of the compound magnesium vanadate. Daily dosage ranges are preferably from about 2 to about 60 mg per kg of patient body weight. Pharmaceutical compositions for use in the method of treatment include magnesium vanadate and at least one pharmaceutically acceptable inert ingredient, and may be oral, parenteral, transdermal or transmucosal dosage forms containing from about 50 to about 1000 mg of magnesium vanadate per unit.

14 Claims, 5 Drawing Sheets

METHOD AND COMPOSITION FOR TREATMENT OF INSULIN RESISTANCE SYNDROMES

This application is a continuation of Ser. No. 08/089,953, filed Jul. 12, 1993, now abandoned.

REFERENCE TO DISCLOSURE DOCUMENT

This application incorporates material included in Disclosure Document No. 306661 filed in the Patent and Trademark Office on Apr. 23, 1992.

BACKGROUND OF THE INVENTION

1. Background of the Prior Art

The invention relates to methods and pharmaceutical compositions for treating diabetes mellitus and other insulin resistance syndromes.

2. Description of the Prior Art

Vanadium is a ubiquitous trace element found in very low concentrations in most living organisms, including human beings. Although it appears to be an essential nutritional element, its specific physiological role has not been conclusively defined. Over the past decade, the biological effects of vanadium have been sought. Vanadium inhibits the activity of various enzymes, particularly the ion transport ATPases, ribonuclease, acid phosphatase and alkaline phosphatase. The effects of vanadium on carbohydrate metabolism have been extensively examined, and vanadium has been found to have profound insulin-like effects.

Vanadium was discovered in 1830. It was used by Lyonnet and colleagues in an attempt to treat several diseases, and was found to decrease glycosuria in patients with diabetes. In the past decade, interest in vanadium was rekindled by the observations that vanadate has a number of insulin-like actions in vitro. These include stimulation of glucose transport into cells (both adipocytes and myocytes), glucose oxidation, glucose storage, glycogen synthesis, and lipogenesis; and inhibition of lipolysis. The effects are rapid and occur within 30 minutes. The actions of vanadium may be related to its ability to enhance phosphorylation of several enzymes and cellular proteins. These actions may be mediated by the stimulation of a vanadium activated cytosolic tyrosine kinase.

In vivo, oral administration of vanadate via drinking water has almost no effect on the glycemia of normal animals, but in diabetic animals causes a dramatic decline in blood glucose to normal or near normal levels without increasing plasma insulin levels. Depending on the studies, insulin levels are either unchanged or decreased. In contrast to the rapid in vitro effects, the in vivo effect is delayed, being seen over the course of several days. In addition to the sustained improvement of blood glucose, the in vivo effects of vanadium include augmentation of muscle and liver glucose uptake and storage, partial weight gain, and improved cardiac performance. The effects have been seen in streptozotocin induced diabetic rats, pancreatectomized diabetic rats, genetically diabetic db/db mice, and obese hyperinsulinemic fa/fa fatty rats.

For the in vivo studies heretofore disclosed in the literature, vanadium has generally been administered as a sodium salt, in the form of either sodium orthovanadate ($Na_3VO_4$) or sodium metavanadate ($NaVO_3$), with the vanadyl salt, vanadyl sulfate trihydrate, also used. These have been given to the test animals in drinking water or in chow. Several protocols describe using a progressively increasing concentration, since the animals appear to have an aversion to the taste of the vanadate salts. Relatively large doses of vanadate have been used since there is poor intestinal absorption of only 1.2%. Typical concentrations in the drinking water have been quite high, e.g., 0.2 to 0.6 mg/ml. It is noted that less sodium metavanadate is required than sodium orthovanadate, possibly because this salt provides 50% more vanadate on a weight basis.

Magnesium is a ubiquitous element in nature, forming 2.1% of the earth's crust. It is an essential nutritional element, the second most abundant intracellular cation in the human body, and has a key role in many metabolic functions. There are many clinical signs, symptoms and disease states attributable to altered magnesium homeostasis. Serum magnesium levels, which are those generally measured, reflect only 1% of the total body magnesium content. Yet, in one study, hypomagnesemia was found in 47% of serum specimens submitted for electrolyte analyses. Magnesium deficiency may be more likely to occur in diabetes mellitus as a consequence of polyuria.

Low levels of intracellular free magnesium have been found in both type II diabetes mellitus and in essential hypertension. Moreover, in patients with essential hypertension, intracellular free magnesium levels have been closely and inversely correlated with both systolic and diastolic blood pressure, and with the integrated plasma insulin response to oral glucose. These observations suggest that the clinical association of hypertension and peripheral insulin resistance (reduced insulin sensitivity) could, in part, be accounted for by magnesium deficiency. Oral magnesium supplementation has been shown to lower blood pressure both in patients with essential hypertension and in individuals with type II diabetes. Ongoing studies are evaluating whether oral magnesium supplementation in either type II diabetes or in essential hypertension is associated with an improvement in insulin sensitivity.

There are many magnesium supplements available in the marketplace, particularly magnesium chloride and magnesium oxide.

Rosetti et al. (Diabetes, 39:1243–50, 1990) studied the effects of lithium and vanadate on glucose metabolism in diabetic rats, and found that rats administered a combination of lithium, vanadate, magnesium and zinc had improved glucose disposal rates in comparison with control groups and groups receiving only lithium and vanadate.

SUMMARY OF THE INVENTION

1. Objects of the Invention

It is the object of the present invention to provide a method and pharmaceutical compositions for the treatment of diabetes mellitus and other insulin resistance syndromes (e.g., obesity, dyslipidemia and hypertension) which may be safely and effectively practiced in human patients.

It is a further object of the present invention to provide methods of treatment and compositions as above described which avoid the need for repeated parenteral administrations.

It is yet another object of the invention to provide pharmaceutical compositions with significant insulinomimetic properties for use in the novel methods of treatment.

2. Brief Description of the Invention

In keeping with these objects and others which will become apparent hereinafter, the invention resides, briefly stated, in a method of treating a human or animal patient suffering from an insulin resistance syndrome, particularly diabetes mellitus, by administering to the patient an effective insulin resistance reducing amount of the compound magnesium vanadate in a pharmaceutical composition additionally containing at least one inert ingredient. The composition is preferably an oral dosage form administered to the patient orally from one to four times daily, but parenteral and other conventional pharmaceutical dosage forms and routes of administration may be used as well in practicing the novel method of treatment.

DETAILED DESCRIPTION OF THE INVENTION

Magnesium vanadate ($MgV_2O_6$), also known as magnesium vanadium oxide, is identified by Chemical Abstracts No. 13573-13-2 and has been disclosed in the prior art as useful, e.g., in corrosion preventive coatings and as a catalyst for chemical reactions such as oxidative dehydrogenation of alkanes. There is no disclosure in the art that magnesium vanadate possesses insulinomimetic properties or would have any utility in treating insulin resistance syndromes.

It has now been discovered that magnesium vanadate is a highly effective pharmaceutical agent for the treatment of insulin resistance syndromes, particularly diabetes mellitus. Animal studies have demonstrated that magnesium vanadate normalizes glucose tolerance in diabetic subjects without increasing plasma insulin concentration, presumably by improving insulin sensitivity and thereby correcting glucose disposal rates. Furthermore, it has been observed that all of the improvement in insulin sensitivity occurs in the glucose storage (glycogen) pathway where the defect in insulin action in human type II diabetes lies.

In accordance with the method of the invention, a human or animal patient suffering from an insulin resistance syndrome (including, but not limited to, diabetes mellitus, obesity, dyslipidemia and hypertension) is treated by the administration of an effective insulin resistance reducing (or insulin sensitivity increasing) amount of magnesium vanadate. The total daily dosage of magnesium vanadate administered to the patient is preferably from about 2 mg to about 60 mg per kilogram of patient body weight, and even more preferably from about 10 to about 40 mg/kg. The daily dosage amount may be administered in one to four equally divided doses. The present invention is not limited, however, to any specific daily dosage range of magnesium vanadate, but instead broadly encompasses the administration of magnesium vanadate as an active pharmaceutical agent to treat insulin resistance syndromes.

The method of the invention may also be used to provide prophylactic magnesium vanadate therapy to patients not yet exhibiting the full-blown symptoms of diabetes mellitus or other insulin resistance syndromes, but who have a predisposition to the development of such conditions. These would include, for example, patients with a family history of diabetes or a personal history of gestational diabetes, obese patients and those exhibiting impaired glucose tolerance. For purposes of the present application, patients having such predispositions are included when reference is made to patients suffering from "an insulin resistance syndrome", and the invention disclosed and claimed herein comprehends the treatment of such patients.

The pharmaceutical compositions used in the subject method may include active ingredients other than magnesium vanadate, for example, other hypoglycemic or anti-hypertensive agents. In particular, it may be of value to co-administer magnesium vanadate and insulin to certain diabetic patients.

The preferred embodiment of the novel method of treatment consists of the administration to the patient of a pharmaceutical composition comprising an effective amount of magnesium vanadate and at least one pharmaceutically acceptable, inert ingredient. The composition may be in any standard pharmaceutical dosage form, but is preferably an orally administered dosage form.

Dosage forms for oral delivery may include conventional tablets, coated tablets, capsules or caplets, sustained release tablets, capsules or caplets, lozenges, liquids, elixirs or any other oral dosage form known in the pharmaceutical arts.

As pharmaceutically acceptable inert ingredients there are contemplated fillers, binders, solvents, etc. which do not interfere with the insulin resistance reducing activity of the magnesium vanadate. Also, fillers such as clays or siliceous earth may be utilized if desired to adjust the size of the dosage form.

Further ingredients such as excipients and carriers may be necessary to impart the desired physical properties of the dosage form. Such physical properties are, for example, release rate, texture and size. Examples of excipients and carriers useful in oral dosage forms are waxes such as beeswax, castor wax, glycowax and carnauba wax, cellulose compounds such as methylcellulose, ethylcellulose, carboxymethylcellulose, cellulose acetate phthalate, hydroxypropylcellulose and hydroxypropylmethylcellulose, polyvinyl chloride, polyvinyl pyrrolidone, stearyl alcohol, glycerin monsterate, methacrylate compounds such as polymethacrylate, methyl methacrylate and ethylene glycol dimethacrylate, polyethylene glycol and hydrophilic gums.

In the compositions of the present invention the magnesium vanadate active ingredient is desirably present in an amount between about 50 and about 1000 mg per dosage unit. The exact dosage administered to each patient will be a function of the condition being treated and the physical characteristics of the patient, such as age and body weight.

Although the oral route of administration is preferred, the present method of treatment also comprehends the administration of magnesium vanadate via the parenteral, transdermal, transmucosal routes or via any other routes of administration known and conventionally utilized in the medical and pharmaceutical arts. Likewise, the compositions of the invention may include magnesium vanadate in pharmaceutically acceptable parenteral, transdermal, transmucosal or other conventional vehicles and dosage forms together with suitable inert solvents, excipients and additives. Many examples of such pharmaceutically acceptable vehicles can be found in *Remington's Pharmaceutical Sciences* (17th edition (1985)) and other standard texts. Whatever route of administration or type of pharmaceutical dosage form is used, the total daily dosage range for the magnesium vanadate active ingredient is preferably from about 2 mg/kg to about 60 mg/kg of patient body weight, although dosage amounts towards the lower end of that range would probably be utilized on parenteral administration.

The method and compositions of the present invention enable safe and effective treatment of patients suffering from insulin resistance syndromes and may avoid the need for such painful and difficult treatments as self-injection of insulin or other regimens which involve potentially serious complications. Moreover, the level of toxicity and side effects upon magnesium vanadate administration should be relatively low.

The Example set forth below describes a study examining the effects of magnesium vanadate on meal tolerance and insulin sensitivity in normal (non-diabetic) and streptozotocin induced diabetic rats in vivo. The Example is not intended, however, to limit or restrict the scope of the invention in any way.

EXAMPLE

PROCEDURE

Figure 1:
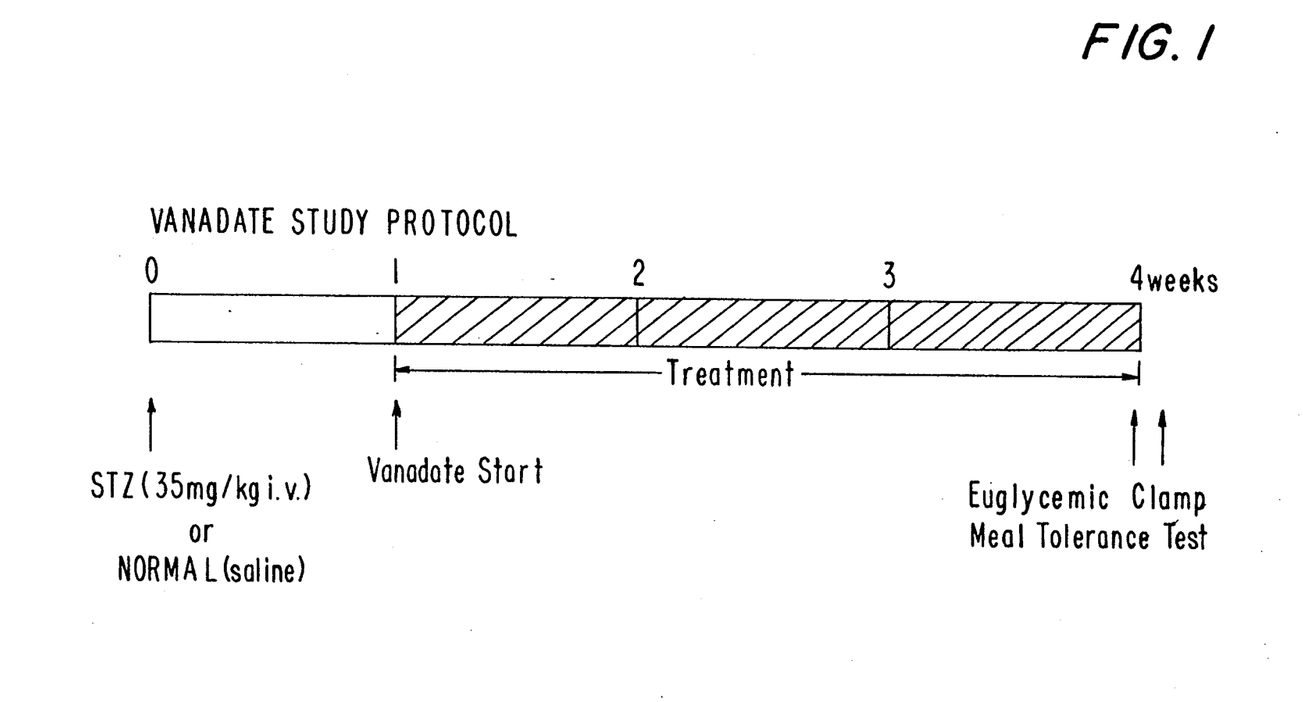
FIG. 1 illustrates the protocol for a study of four groups of rats: an untreated control group of normal rats, a control group treated with magnesium vanadate, and two groups of streptozotocin-induced diabetic rats, one untreated and one treated with magnesium vanadate.

Four groups of Sprague-Dawley rats (Charles River, Wilmington, Mass.) were studied: group 1, controls (n=4); group 2, controls treated with magnesium vanadate (n=4); group 3, streptozotocin induced diabetic rats treated with magnesium vanadate (n=8); group 4, streptozotocin induced diabetic rats treated with magnesium vanadate (n=8) (Table 1). The study design is shown in FIG. 1. Streptozotocin (35 mg/kg body weight) was prepared in citrate buffer (0.05M. pH 5.5) and injected into the tail vein of rats weighing 150-200 g (~8 weeks of age). Control rats received an injection of normal saline into the tail vein. Only rats whose post prandial tail vein glucose levels were more than 200 mg/dl on two different occasions were studied in groups 3 and 4. Two thirds of the rats which received 35 mg/kg streptozotocin reached this criteria.

One week after the streptozotocin injection, magnesium vanadate (0.2-0.35 mg/ml in drinking water, Cerac Inc., Milwaukee, Wis.) treatment was initiated. Magnesium vanadate was dissolved in doubled distilled water without adding sodium chloride. The vanadate concentration in the drinking water was adjusted every 3 days to maintain the post-prandial plasma glucose level between 100 and 150 mg/dl. Rats were housed in individual cages and subjected to a standard light (6:00 a.m. to 6:00 p.m.)-dark (6:00 p.m. to 6:00 a.m.) cycle and were given regular rat chow. Water and food intake was measured every day. Tail vein blood was collected for the measurement of fed plasma glucose concentration twice a week (8:00 a.m.).

Two weeks after the vanadate treatment, rats were anesthetized with an injection of pentobarbital (50 mg/kg/body weight i.p.) and indwelling catheters were inserted into the right internal jugular vein and the left carotid artery. Four days after insertion of the catheters, rats received a meal tolerance test. At 8:00 a.m. after an overnight fast, rats spontaneously consumed 2 gram of rat chow over 5-10 minutes. Blood was collected from the tail vein at time 0, 60 and 120 minutes for the determination of plasma glucose and insulin concentrations.

Six days after the catheter insertion, rats received a euglycemic insulin clamp. Insulin was given as a prime-continuous (12 mU/kg/min) infusion. Simultaneously with the start of insulin, a prime (2.0 $\mu$Cl) continuous (0.15 $\mu$Cl) infusion of 3-$^3$H-glucose was given via the carotid artery. For diabetic rats in group 3, the priming dose of tritiated glucose was increased by one third. During the insulin clamp the plasma glucose concentration was maintained at ~100 mg/dl by the variable infusion of a 25% glucose solution. Plasma samples were obtained at 5 minute intervals during the last 20 minutes of the insulin clamp for determination of tritiated glucose specific activity and tritiated water radioactivity. At the end of the 120 minute study, rats were injected with pentobarbital (60 mg/kg body weight), the abdomen was quickly opened and the rectus abdominalis muscle, liver, kidney, heart and hindlimb muscles were removed and freeze-clamped with aluminum tongs precooled in liquid nitrogen. All tissue samples were stored at ~80° C. A urine sample was obtained at the end of the insulin clamp.

Plasma glucose was measured by the glucose oxidase method (Beckman Glucose Analyzer, Beckman Instruments, Palo Alto, Cal.). Plasma insulin was measured by radioimmunoassay using rat insulin antibody and rat insulin standard (Linco, St. Louis, Mo.). Plasma tritiated glucose radioactivity was measured on the supernatants of barium hydroxide-zinc sulphate precipitates (Somogyl procedure) of plasma samples after evaporation of tritiated water.

Total body glucose disposal during the last 20 minutes of the insulin clamp was calculated by adding the glucose infusion rate and the residual rate of hepatic glucose production. the rate of hepatic glucose production was calculated by subtracting the cold glucose infusion rate from the tracer derived rate of glucose appearance during the last 20 minutes of the insulin clamp. Total glycolytic flux was calculated from the tritiated water production rate, assuming the water distribution volume was 65% of rat body weight. The rate of total body glycogen synthesis was determined by subtracting the glycolytic rate from the rate of total body glucose disposal during the last 20 minutes of the insulin clamp.

All values are expressed as the mean ±SEM. Comparisons between groups was performed by ANOVA.

Figure 5:
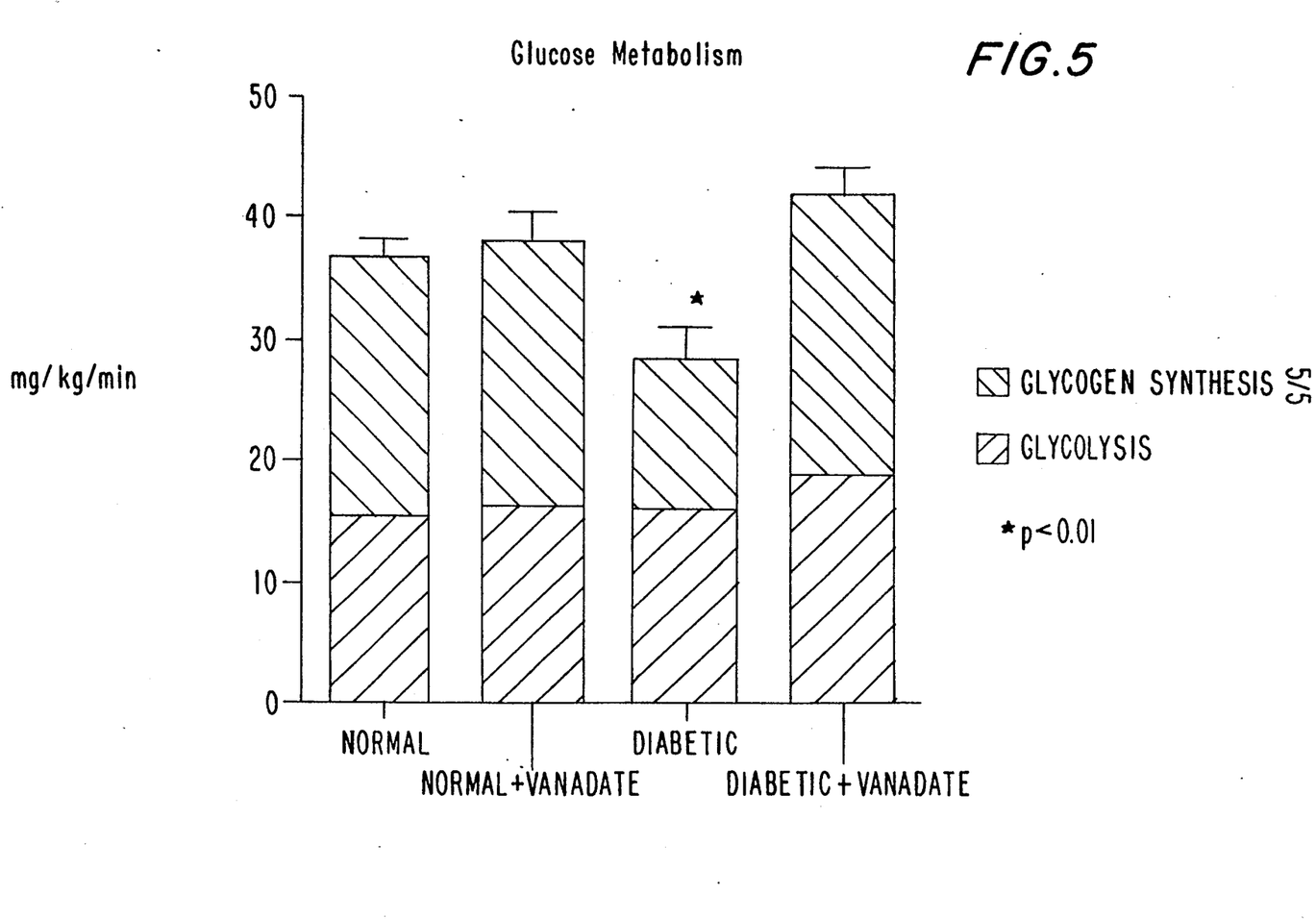
FIG. 5 is a bar graph illustrating rates of glucose metabolism, shown in components of glycogen synthesis and glycolysis, for all four groups of rats upon receiving a continuous insulin infusion via a euglycemic clamp.

RESULTS gen synthesis and this was restored to values slightly greater than in controls following vanadate treatment (FIG. 5 and Table 2). A significant increase in glycolysis also was observed in diabetic rats following vanadate treatment.

TABLE 1

| | Group | Body Weight (gm) | Increase in Body weight (g/day) | Food (g/day) | Water (ml/day) |
|---|---|---|---|---|---|
| I. | Normal (n = 4) | 316 ± 11 | 7.8 ± 0.5 | 27.6 ± 1.0 | 37.8 ± 2.9 |
| II. | Normal + Vanadate (n = 4) | 241 ± 5* | 4.7 ± 0.6* | 27.1 ± 1.7 | 24.1 ± 1.2 |
| III. | Diabetic (n = 8) | 270 ± 19* | 3.5 ± 0.7* | 38.5 ± 2.4 | 126.3 ± 17.3* |
| IV. | Diabetic + Vanadate (n = 8) | 254 ± 13* | 2.9 ± 0.5* | 26.4 ± 2.8 | 28.7 ± 2.4 |

*$p < 0.05$ vs Normal

TABLE 2

| | Insulin Mediated Glucose Metabolism | | | | |
|---|---|---|---|---|---|
| | Total Glucose Disposal (mg/kg/min) | Hepatic Glucose Production (mg/kg/min) | Glycolysis (mg/kg/min) | Glycogen Synthesis (mg/kg/min) | Plasma Insulin Conc. (μU/ml) |
| Normal | 36.8 ± 0.8 | 0.3 ± 1.0 | 15.3 ± 0.5 | 21.5 ± 0.3 | 140 ± 4 |
| Normal + Vanadate | 38.0 ± 2.2 | −2.7 (0) ± 1.1 | 16.2 ± 0.5 | 21.8 ± 2.7 | 123 ± 11 |
| Diabetic | 28.3 ± 3.0* | 3.1 ± 1.2 | 15.9 ± 1.4 | 12.5 ± 2.2* | 125 ± 12 |
| Diabetic + Vanadate | 41.8 ± 2.2* | −2.9 (0) ± 1.5 | 18.8 ± 1.4* | 23.0 ± 2.1 | 129 ± 16 |

*$p < 0.05$ vs Normal

Figure 2A:
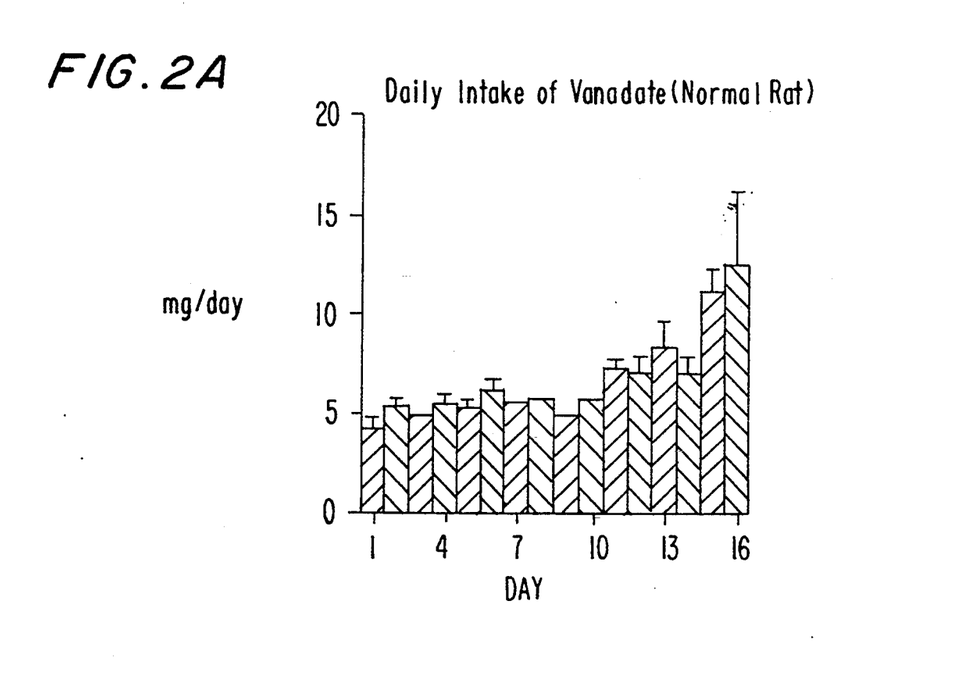
FIG. 2A is a bar graph illustrating the daily intake of magnesium vanadate in the control group of normal rats.
Figure 2B:
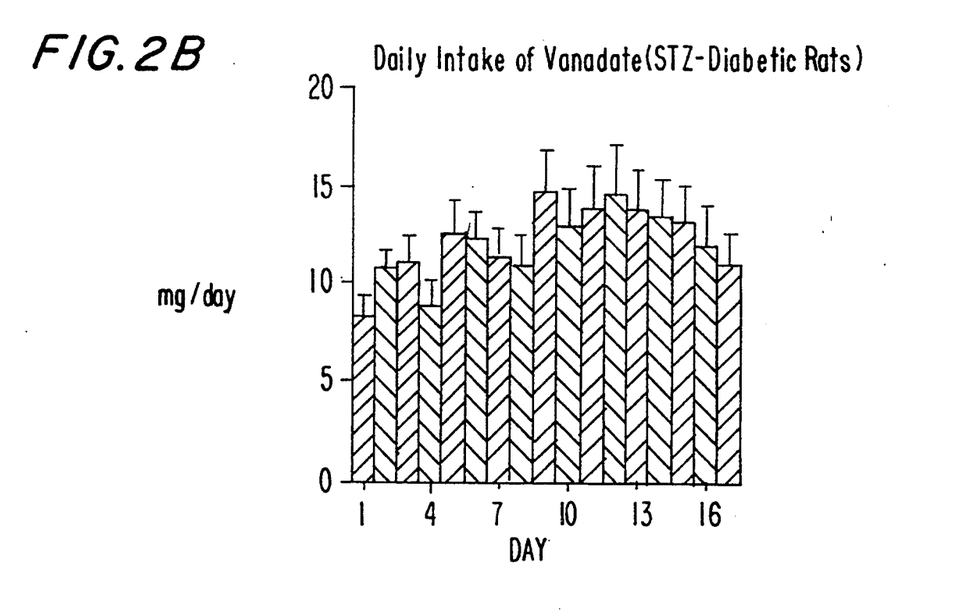
FIG. 2B is a bar graph illustrating the daily intake of magnesium vanadate in the group of streptozotocin-induced diabetic rats.

In normal (group 2) and diabetic (group 4) rats, the magnesium vanadate concentration in drinking water was initiated with 0.2 mg/ml and increased to 0.5-0.6 mg/ml. The daily intake of vanadate for the control and diabetic rats during the three week treatment period is shown in FIG. 2. For most of the three week treatment period diabetic rats consumed twice as much vanadate as controls. Body weight, average daily food intake, and water intake are summarized in Table 1. Control rats treated with vanadate gained less weight and consumed less water than those rats not treated with vanadate. Food intake was similar in these two groups. Diabetic rats treated with vanadate consumed less food and water than diabetic rats receiving no vanadate; weight gain was similar in both diabetic groups.

Figure 3A:
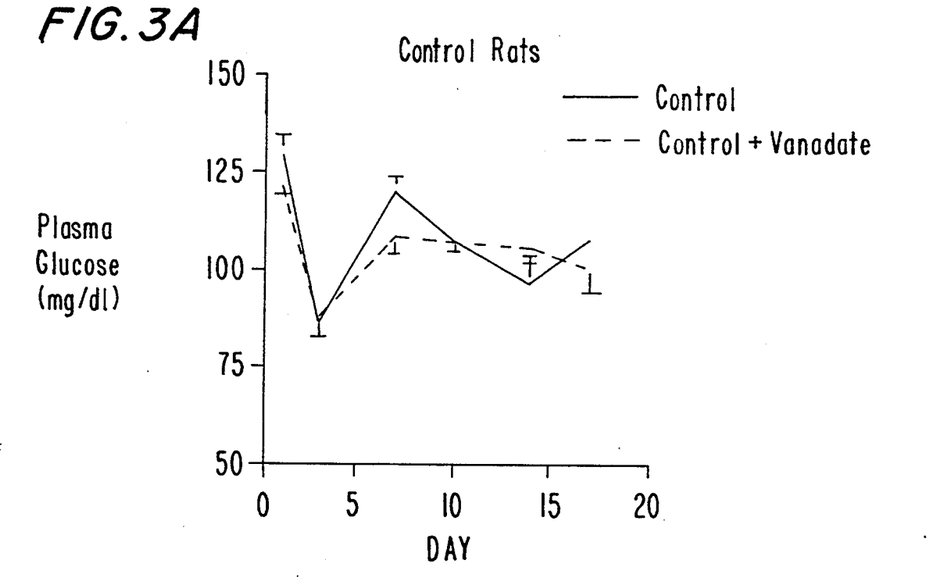
FIG. 3A is a graph of fed plasma glucose concentrations versus time (days) in the two control groups of normal rats, one untreated and one treated with magnesium vanadate.
Figure 3B:
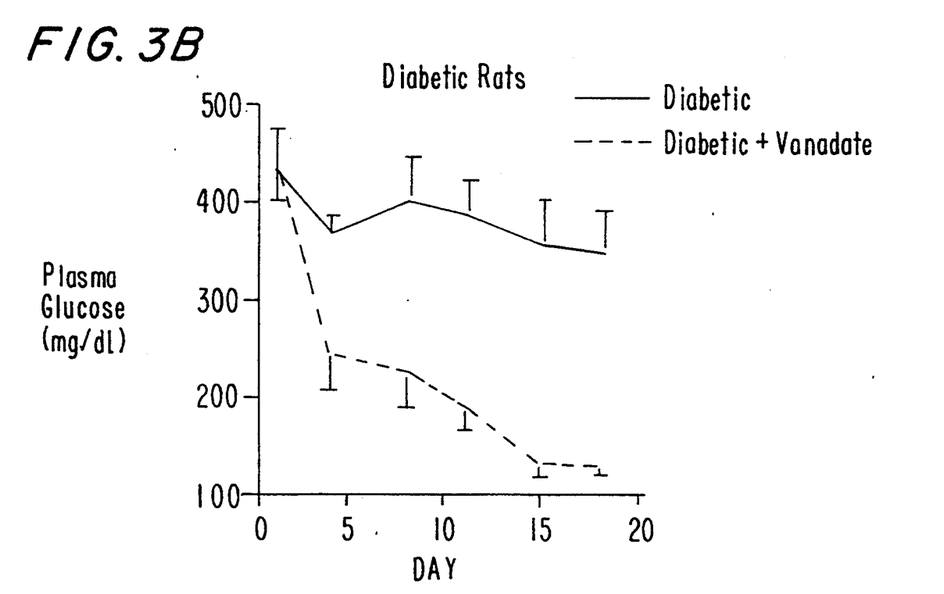
FIG. 3B is a graph of fed plasma glucose concentrations versus time (days) in the two groups of diabetic rats, one untreated and one treated with magnesium vanadate.

Fed plasma glucose concentration in groups 1 and 2 during the three week study period were similar (FIG. 3A). Fed plasma glucose concentrations in group 3 (STZ-diabetic rats) remained between 375-425 mg/dl, while STZ-diabetic rats treated with magnesium vanadate (group 4) had significantly lower glucose levels (<150 mg/dl) (FIG. 3B).

Figure 4A:
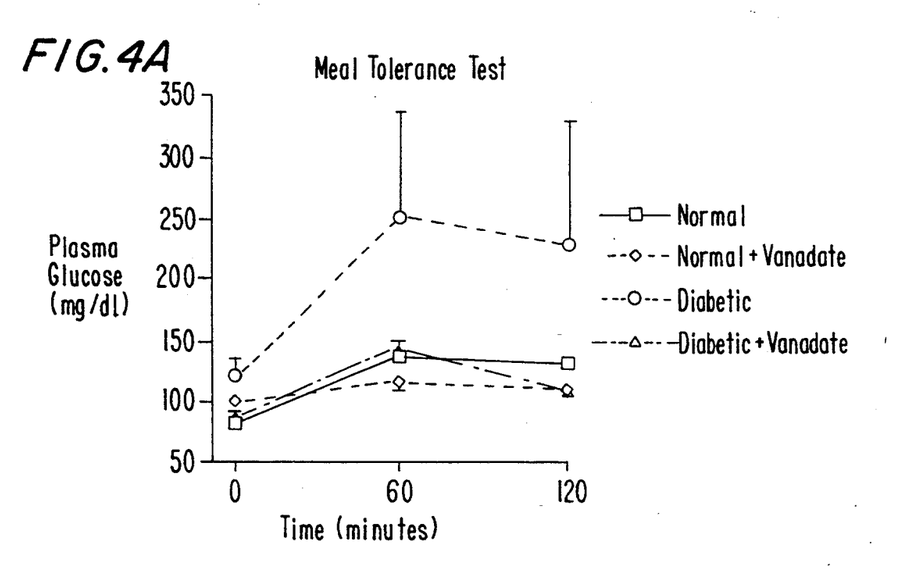
FIG. 4A is a graph of fasting and one hour and two hour post-meal plasma glucose levels in all four study groups of rats.
Figure 4B:
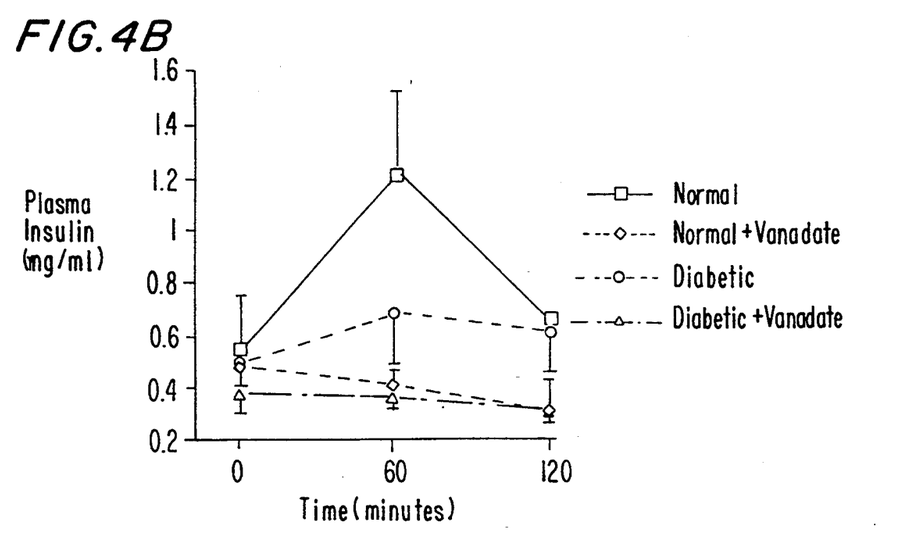
FIG. 4B is a graph of fasting and one hour and two hour post-meal plasma insulin levels in all four study groups of rats.

Results of the meal tolerance test are shown in FIG. 4. Fasting, one hour, and two hour post-meal plasma glucose levels were significantly decreased in STZ-diabetic rats compared to controls (FIG. 4A). Following vanadate treatment diabetic rats demonstrated normal oral tolerance without any increase in plasma insulin response (FIG. 4B).

Plasma insulin levels during the euglycemic insulin clamp studies were similar in all four groups (Table 2). During the last 20 minutes of 12 mU/kg/min euglycemic insulin clamp, glucose metabolism was significantly decreased in diabetic versus normal rats (28.3±3.0 vs 36.8±0.8 mg/kg/min) and was returned to values greater than in normals after vanadate treatment (41.8±2.2 mg/kg/min). Vanadate treatment had no effect on insulin-mediated glucose disposal in normal rats (38.0±2.2 mg/kg/min). In diabetic rats all of the insulin resistance was accounted for by impaired glycogen synthesis and this was restored to values slightly greater than in controls following vanadate treatment (FIG. 5 and Table 2). A significant increase in glycolysis also was observed in diabetic rats following vanadate treatment.

It has thus been shown that there are provided methods and compositions which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims.

We claim:

1. A method of treating a human or animal patient suffering from an insulin resistance syndrome, said method comprising the administration to the patient of an effective insulin resistance reducing amount of magnesium vanadate.

2. A method according to claim 1 wherein said syndrome is selected from the group consisting of diabetes mellitus, obesity, dyslipidemia and hypertension.

3. A method according to claim 2 wherein said syndrome is diabetes mellitus.

4. A method according to claim 1 wherein said patient is human.

5. A method according to claim 1 wherein said effective amount of magnesium vanadate is from about 2 to about 60 miligrams per kilogram of patient body weight per day.

6. A method according to claim 5 wherein said effective amount is from about 10 to about 40 milligrams per kilogram of patient body weight per day.

7. A method according to claim 5 wherein said effective amount is administered to the patient in one to four divided doses.

8. A method according to claim 1 wherein the magnesium vanadate is administered to the patient in a pharmaceutical composition which additionally includes at least one pharmaceutically acceptable inert ingredient.

9. A method according to claim 8 wherein said pharmaceutical composition is administered orally.

10. A method according to claim 9 wherein said pharmaceutical composition is an oral dosage form selected from the group consisting of tablets, coated tablets, capsules, caplets, sustained release tablets, capsules or caplets, liquids and elixirs.

11. A method according to claim 8 wherein said pharmaceutical composition is administered parenterally, transdermally or transmucosally.

12. A method according to claim 8 wherein said composition includes an additional pharmaceutically active ingredient.

13. A method according to claim 12 wherein said additional active ingredient is selected from the group consisting of hypoglycemic agents and antihypertensive agents.

14. A method according to claim 13 wherein said additional active ingredient is insulin.

* * * * *